US006221036B1

(12) United States Patent
Lucas

(10) Patent No.: US 6,221,036 B1
(45) Date of Patent: Apr. 24, 2001

(54) SUPPORT FOR A LIMB OF A BODY

(76) Inventor: Thomas E. Lucas, 505 Kiesel Ave., Ogden, UT (US) 84404

( * ) Notice: Subject to any disclaimer, the term of this patent is extended or adjusted under 35 U.S.C. 154(b) by 0 days.

(21) Appl. No.: 09/045,775

(22) Filed: Mar. 19, 1998

(51) Int. Cl.[7] .............................. A61F 5/00; A47C 20/02; A61G 15/00

(52) U.S. Cl. ................................ 602/23; 602/5; 128/845; 5/648

(58) Field of Search .................................... 602/5, 23, 20, 602/60–62, 32, 33, 36; 128/846, 878, 882, 845; 297/440.11; 5/625, 627, 628, 648, 624; D12/128

(56) References Cited

U.S. PATENT DOCUMENTS 2,630,288 * 3/1953 Eubanks, Sr. ........................ 248/118
2,722,692 * 11/1955 Dempster ................................ 5/646
3,066,322 * 12/1962 Derby ................................ 601/63 X
5,027,799 * 7/1991 Laico et al. ............................ 602/20
5,111,808 * 5/1992 Meals .................................... 602/23
5,716,101 * 2/1998 Frinier et al. ............... 297/440.11 X

FOREIGN PATENT DOCUMENTS

14195 * 7/1916 (GB) .............................. 297/440.11

* cited by examiner

*Primary Examiner*—Mickey Yu
*Assistant Examiner*—Denise Pothier
(74) *Attorney, Agent, or Firm*—Thompson E. Fehr

(57) ABSTRACT

A support for a limb of a body having a sheet of flexible material with longitudinal loops running along the sides of such sheet. The longitudinal loops can readily, but releasably and securely, be attached, with rods, to the sides of a base for the support. Optionally, the sides of the base will be higher at one end of the support than at the other end in order to improve comfort for a user. Also, optionally the distance of the tops of the sides from the bottom of the base is adjustable.

3 Claims, 10 Drawing Sheets

SUPPORT FOR A LIMB OF A BODY

BACKGROUND OF THE INVENTION

1. Field of the Invention

This invention relates to a device for elevating a limb of a body, which elevation is primarily used as part of the curative process for a limb that has been sprained or fractured or which suffers from a disease such as gout, arthritis, varicose veins, edema, or the like.

2. Description of the Related Art

The traditional means for accomplishing such suspension utilizes a cable attached to the limb and then running across an elevated pulley. This process is so cumbersome that it is difficult for the patient, himself or herself, to adjust the suspension cable. Furthermore, the pulley generally allows very little freedom of lateral (as opposed to vertical and longitudinal) movement, ie., movement is substantially restricted about the yaw axis. Similarly little longitudinal movement can be attained.

A number of inventions have, however, been patented for accomplishing the requisite suspension by supporting the limb on a sheet of material, preferably fabric. Other related patients apply to devices that are not intended for the support of a limb but could be so utilized.

These prior inventions, however, fall into three categories.

The first category includes patented devices where the sheet could become dislodged from the supporting base relatively easily. Composing this category are U.S. Pat. Nos. 2,630,288; 2,722,692; 3,742,532; and 5,111,808.

Patents within the second category are those covering devices where the sheet cannot be removed from the supporting base. These patents are U.S. Pat. Nos. 1,195,917 (One of two sheets utilized in the device of this patent can, however, be removed.); 2,244,440; 2,785,418; 2,834,032; 3,294,451; 3,430,956; and 4,544,203.

Devices within the third category of patents secure the sheet to the supporting base built do so in a manner which would require a substantially long time wither to remove or to install the sheet. This third category is composed of U.S. Pat. Nos. 2,020,262; 2,735,480; 3,066,322; 3,086,225; and 3,472,224.

SUMMARY OF THE INVENTION

The present invention includes a sheet which has loops formed along the longitudinal sides of the sheet. On each longitudinal side of the sheet, a rod is inserted into the loop or loops. Each rod is then releasably, but securely and readily, attached to one longitudinal side of the supporting base.

DESCRIPTION OF THE PREFERRED EMBODIMENT

Figure 1:
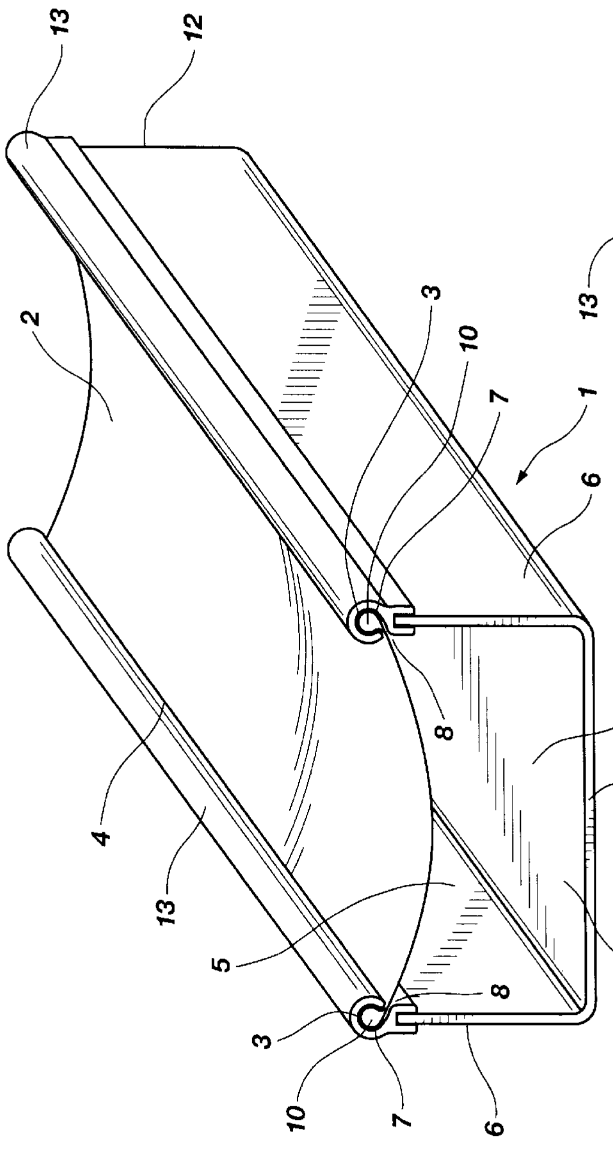
FIG. 1 depicts an isometric view of the preferred embodiment for the Support for a Limb of a Body.
Figure 3:
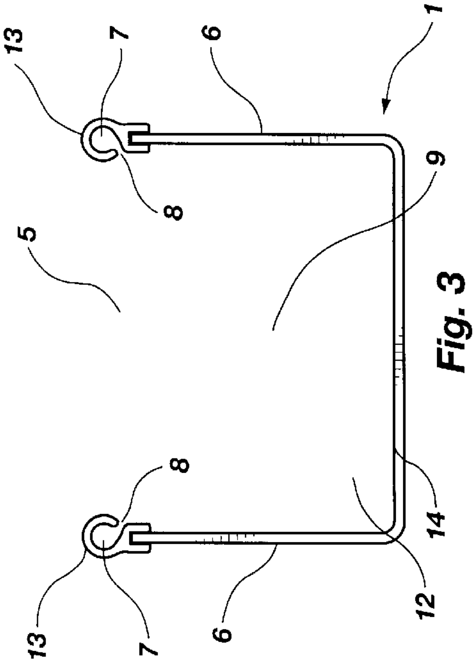
FIG. 3 provides a view from the higher end of the Support for a Limb of a Body.

As illustrated in FIG. 1 and FIG. 3, the preferred embodiment of the Support for a Limb of a Body has a base 1 with a generally U-shaped cross section.

A sheet 2 of flexible material, preferably fabric, has loops 3 formed, preferably by stitching, along the longitudinal sides 4 of the sheet 2.

At the open top 5 of the base 1, each side 6 of the base 1 widens to contain a channel 7 having a slot 8 opening toward the center 9 of the base 1. A rod 10, which is preferably composed of a plastic material, is inserted into one of the loops 3 of the sheet 2; and a similar rod 10 is inserted into the other of the loops 3 of the sheet 2. One rod 10 and the corresponding loop 3 of the sheet 2 are inserted into one channel 7, with the sheet extending through the slot 8. The other rod 10 and the corresponding loop 3 of the sheet 2 are inserted into the other channel 7, with the sheet extending through the slot 8. Thus, the loops 3 and rods 10 can readily be placed into the channels 7; and frictional forces releasably but securely retain the loops 3 and rods 10 within the channels 7 when a limb of a body is placed on and moves upon the sheet 2.

Figure 2:
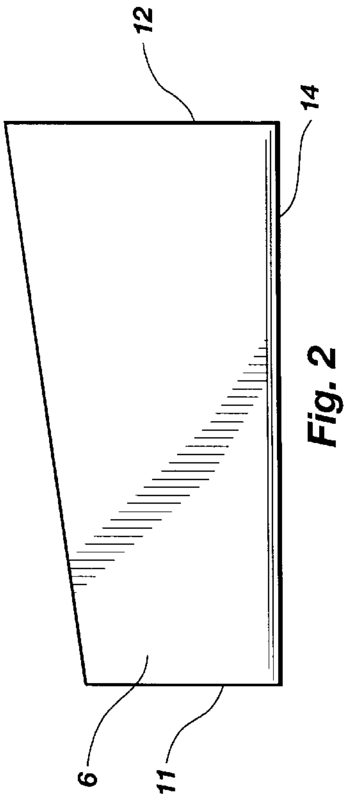
FIG. 2 shows the preferred embodiment for the Support for a Limb of a Body from the side.

Preferably, as illustrated in FIG. 1, FIG. 2, and FIG. 3, the sides 6 of the base 1 rise as they move from a first end 11 toward a second end 12 of the base 1. This increases the comfort for a user of the Support for a Limb of a Body when the distal end of the limb is placed beyond the first end 11 of the base 1 before approaching or passing the second end 12 of the base 1.

Rather than simply widening each side 6 of the base 1, a separate tube 13 containing the channel 7 and having a slot 8 can be attached to the top 5 of each side 6 of the base 1 and oriented so that the slot 8 opens toward the center 9 of the base 1.

Optionally, the preferred embodiment can have the distance between the bottom 14 of the base 1 and the channel 7 be adjustable. An auxiliary side 17 is located adjacent to each side 6 and slidably but lockably attached to each side 6, preferably as described below.

Figure 5:
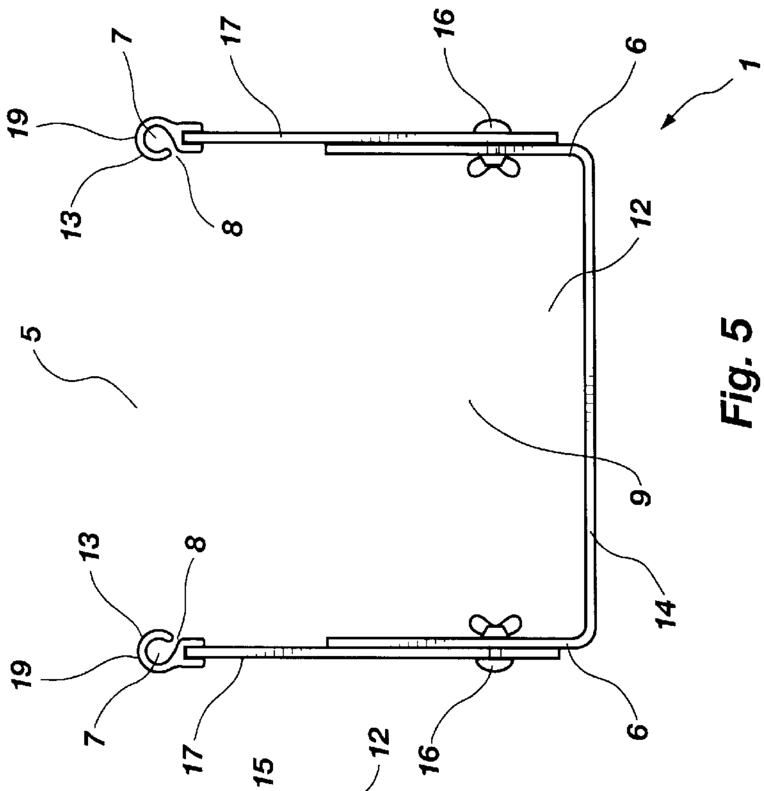
FIG. 5 gives a view from the higher end of the adjustable version of the preferred embodiment of the Support for a Limb of a Body.
Figure 4:
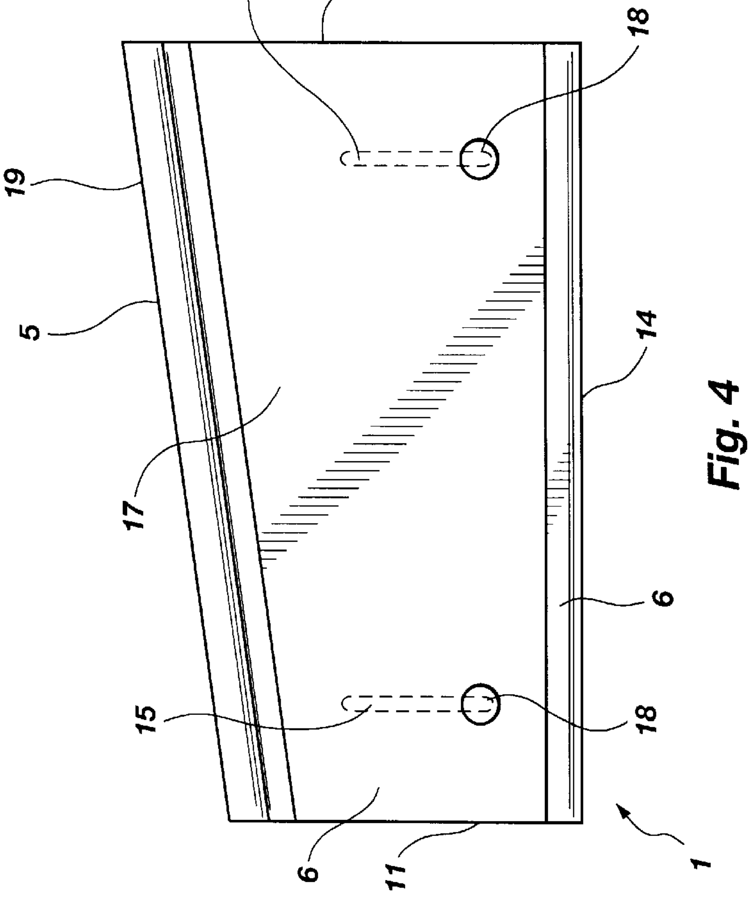
FIG. 4 is a side view of an adjustable version of the preferred embodiment of the Support for a Limb of a Body.
Figure 6:
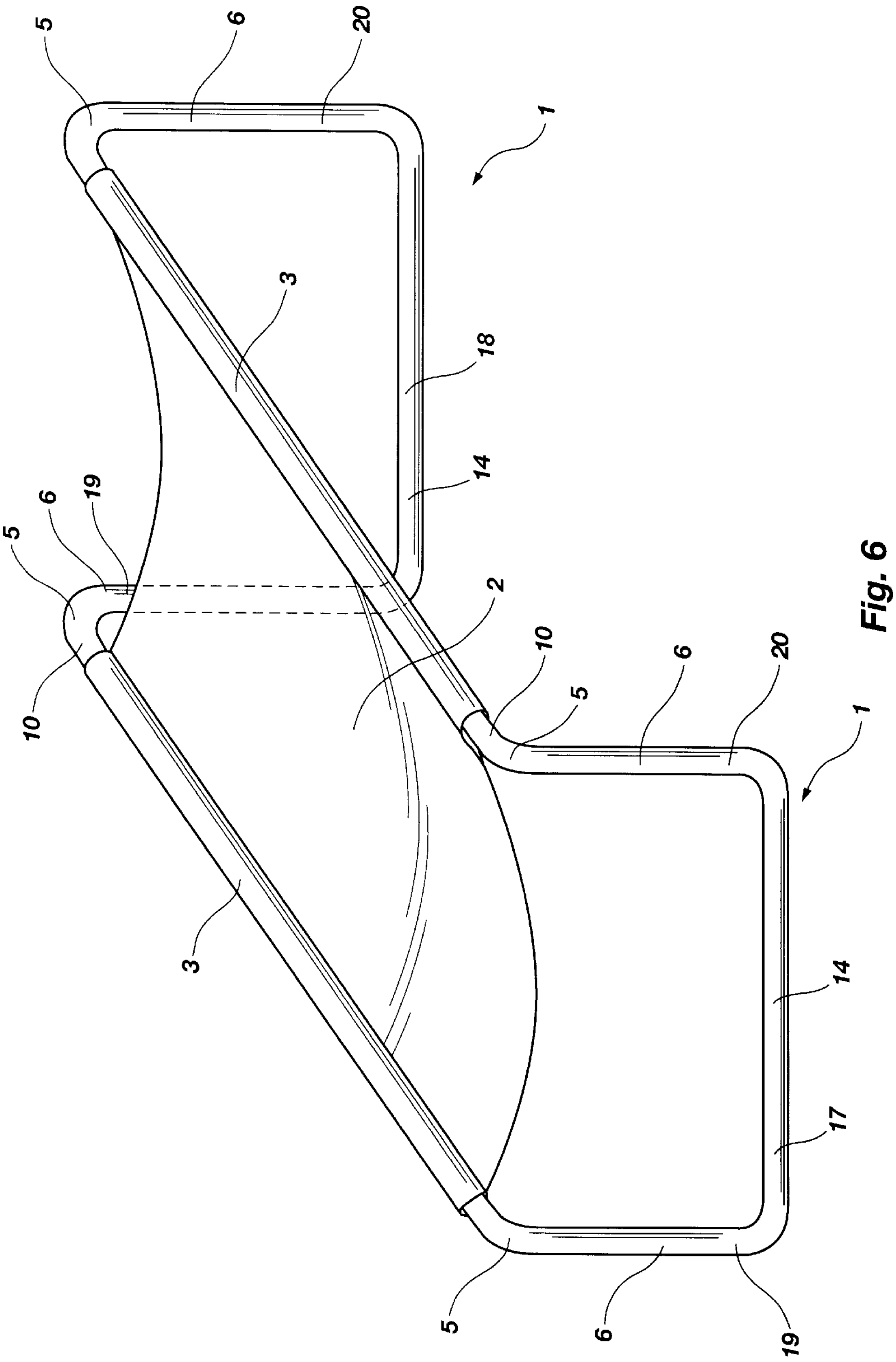
FIG. 6 depicts an isometric view of an alternate embodiment for the Support for a Limb of a Body where the rods and bases are combined into a single tube.
Figure 9:
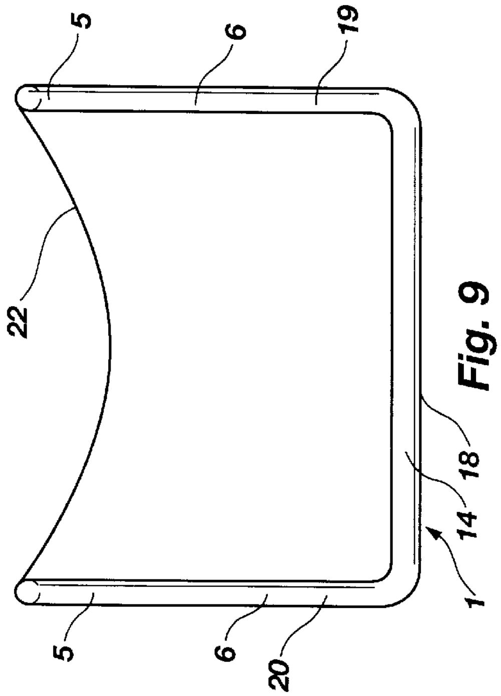
FIG. 9 provides a view from the higher end of the embodiment of FIG. 6.
Figure 7:
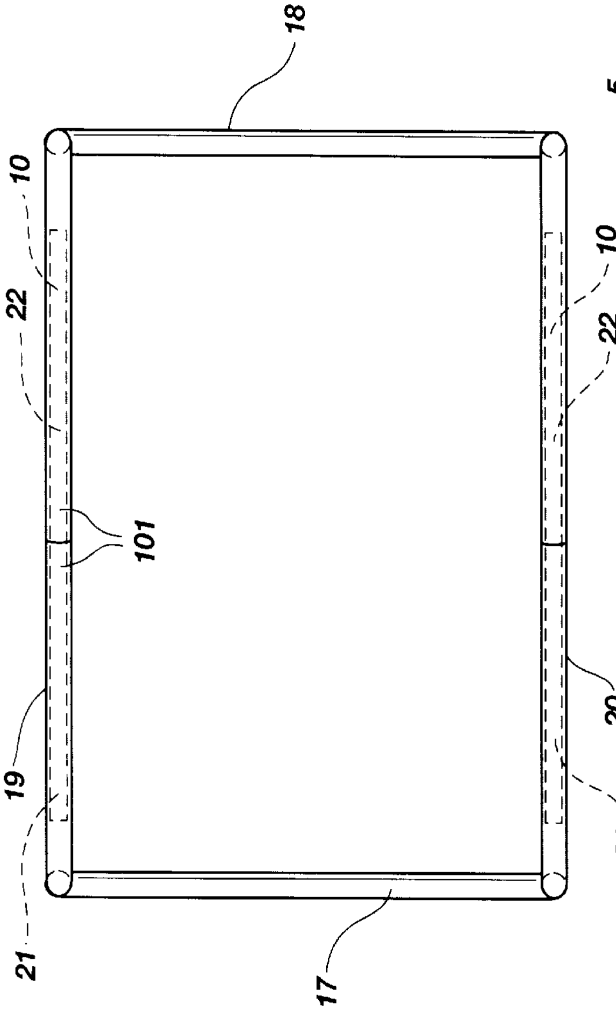
FIG. 7 shows the embodiment of FIG. 6 from the top, without the sheet.
Figure 8:
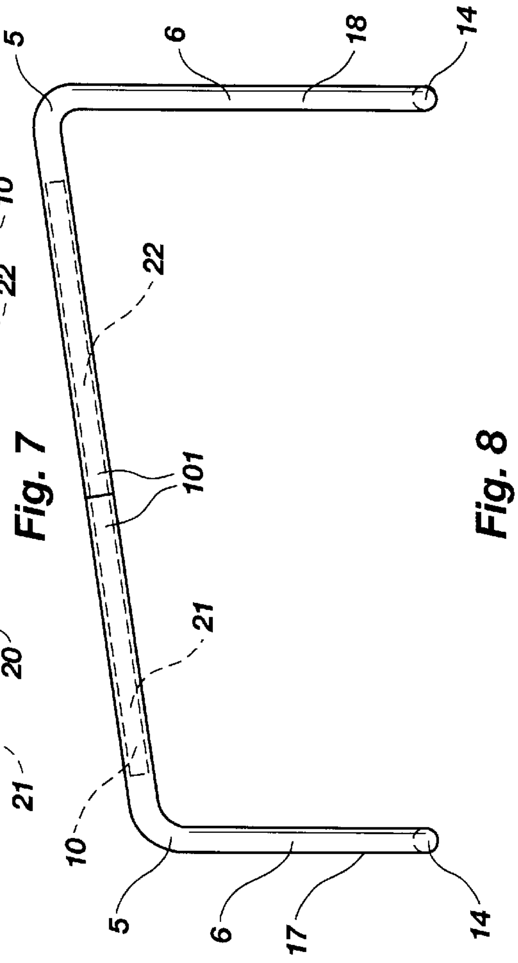
FIG. 8 is a side view of the embodiment of FIG. 6, without the sheet.

Preferably, as illustrated in FIG. 4 and FIG. 5, each side 6 of the base 1 will be of generally uniform width throughout its length and will contain one or more slots 15 to accommodate a releasable fastener 16, such as a bolt and wing nut. Each auxiliary side 17 contains one or more apertures 18 to accommodate a releasable fastener 16. At the top 19 of each auxiliary side 17, either the auxiliary side 17 widens to accommodate the channel 7 having the slot 8 or, optionally, a separate tube 13 containing the channel 7 and having a slot 8 is attached to the auxiliary side 17. The releasable fastener 16 is simply released to allow the auxiliary side 17 to be moved up or down with respect to the corresponding side 6; and when the desired distance has been reached, the releasable fastener 16 is again fastened.

An optional embodiment of the Support for a Limb of a Body is depicted in FIG. 6, FIG. 7, FIG. 8, and FIG. 9.

This first optional embodiment has a base 1 which consists of a first end 17 and a second end 18. The bottom 14 of the base 1 is preferably a hollow tube, as the sides 6 also are. At the first end 17 of the base 1, one side 6 is attached on a first side 19 of the base 1 and another side 6 is attached on a second side 20 of the base 1; at the second end 18 of the base 1, one side 6 is attached on a first side 19 of the base 1 and another side 6 is attached on a second side 20 of the base 1. A rod 10 is connected to the top 5 of a side 6 at the first end 17 of the base 1 on the first side 19 of the base 1; the rod 10 then runs to the second end 18 of the base 1 on the first side 19 of the base 1, where the rod 10 is connected to the top 5 of a side 6. Similarly, another rod 10 is connected to the top 5 of a side 6 at the first end 17 of the base 1 on the second side 20 of the base 1; the rod 10 then runs to the second end 18 of the base 1 on the second side 20 of the base 1, where the rod 10 is connected to the top 5 of a side 6.

The sides 6 at the second end 18 of the base 1 are preferably longer than are the sides 6 at the first end 17 of the base 1.

The rods 10 are preferably hollow tubes. Between the first end 17 of the base 1 and the second end 18 of the base 1, each rod 10 can be separated into a first portion 21 and a second portion 22. First portion 21 is releasably connected to second portion 22 for each rod 10. Preferably, a connecting bar 101 having an outer diameter which is smaller than the inner diameter of the rod 10 is permanently attached to the inside of the first portion 21 of the rod 10 and extends from the first portion 21 of the rod 10. Then the second portion 22 of the rod 10 simply slides over the exposed portion of the connecting bar to become removably attached to the first portion 21 of the rod 10. The inner diameter of the rod 10 and the outer diameter of the connecting rod are chosen so that the frictional force between the rod 10 and the connecting rod will be sufficiently great to prevent inadvertent separation of the longitudinal bar from the connecting rod but sufficiently low that an average person can intentional separate and connect the longitudinal bar and the connecting rod, i.e., the first portion 21 of the rod 10 is readily, but releasably and securely, connected to the second portion 22 of the rod 10.

Of course, to assemble this first optional embodiment, the first portion 21 of each rod 10 is separated from the second portion 22 of each rod 10. Then the loops 3 of the sheet 2 are pushed onto either the first portion 21 or the second portion 22, and the first portion 21 is readily, but releasably and securely, connected to the second portion 22 of the corresponding rod 10 so that the sheet 2 is readily, but releasably and securely, attached to the base 1.

Figure 12:
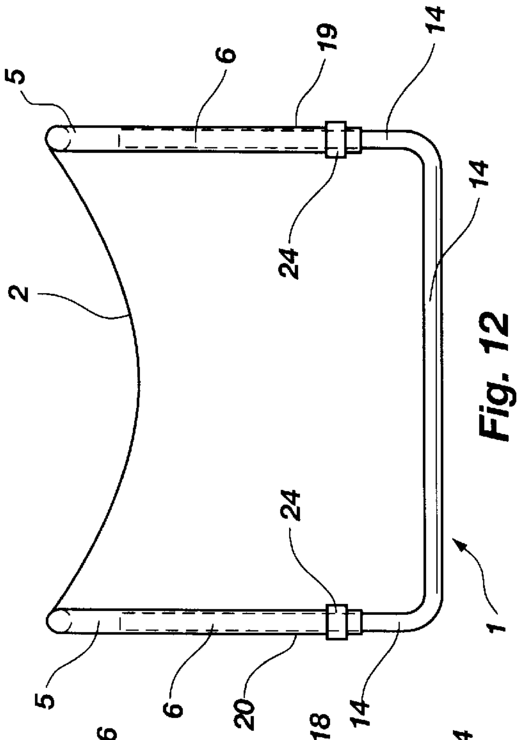
FIG. 12 provides a view from the higher end of the embodiment of FIG. 6 where the height of the base is adjustable.
Figure 11:
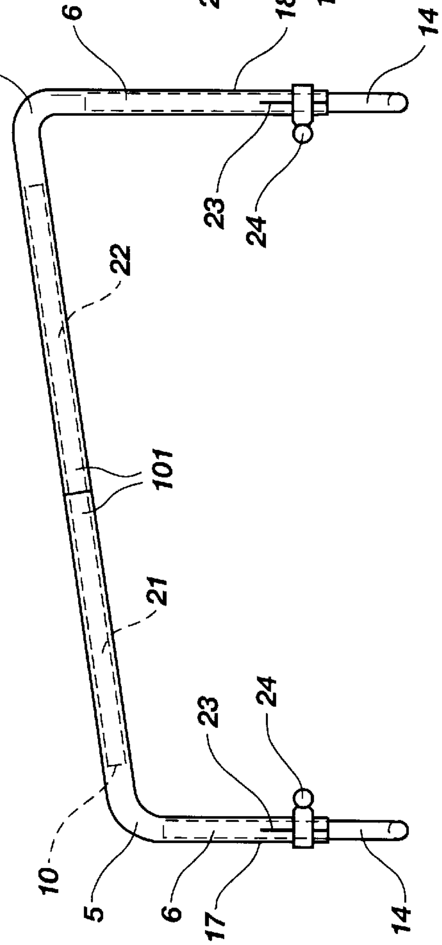
FIG. 11 is a side view of the embodiment of FIG. 6 where the height of the base is adjustable.
Figure 10:
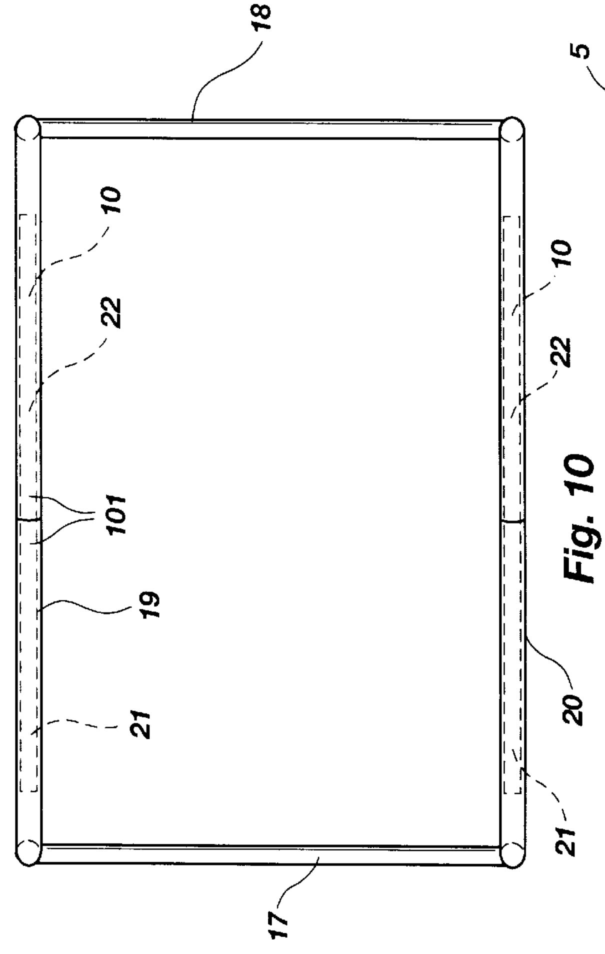
FIG. 10 shows, from the top, the embodiment of FIG. 6 where the height of the base is adjustable.
Figure 13:
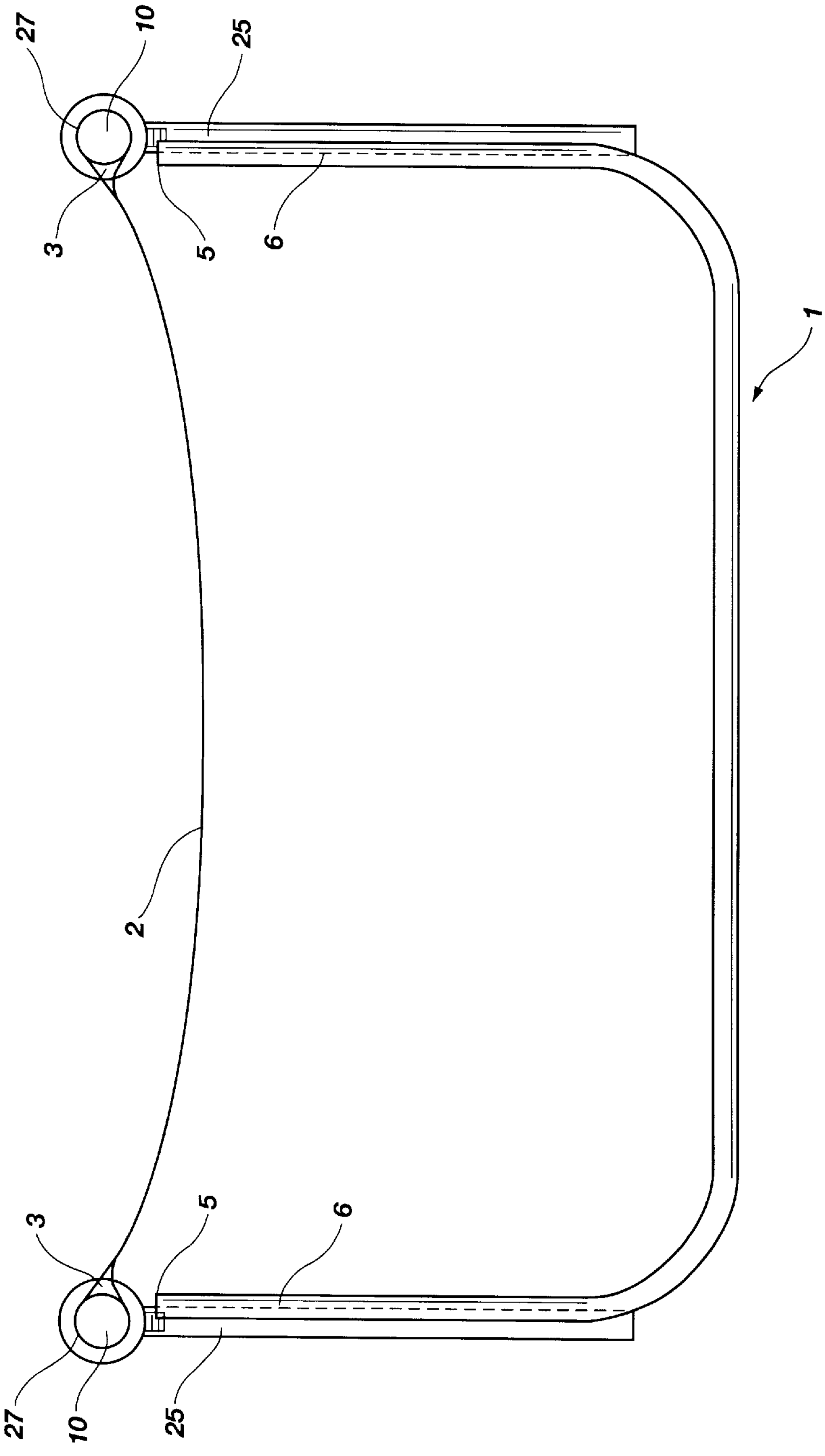
FIG. 13 is an end view of an embodiment similar to that of FIG. 1 except that an alternate means is employed to attach the sheet to the base.
Figure 14:
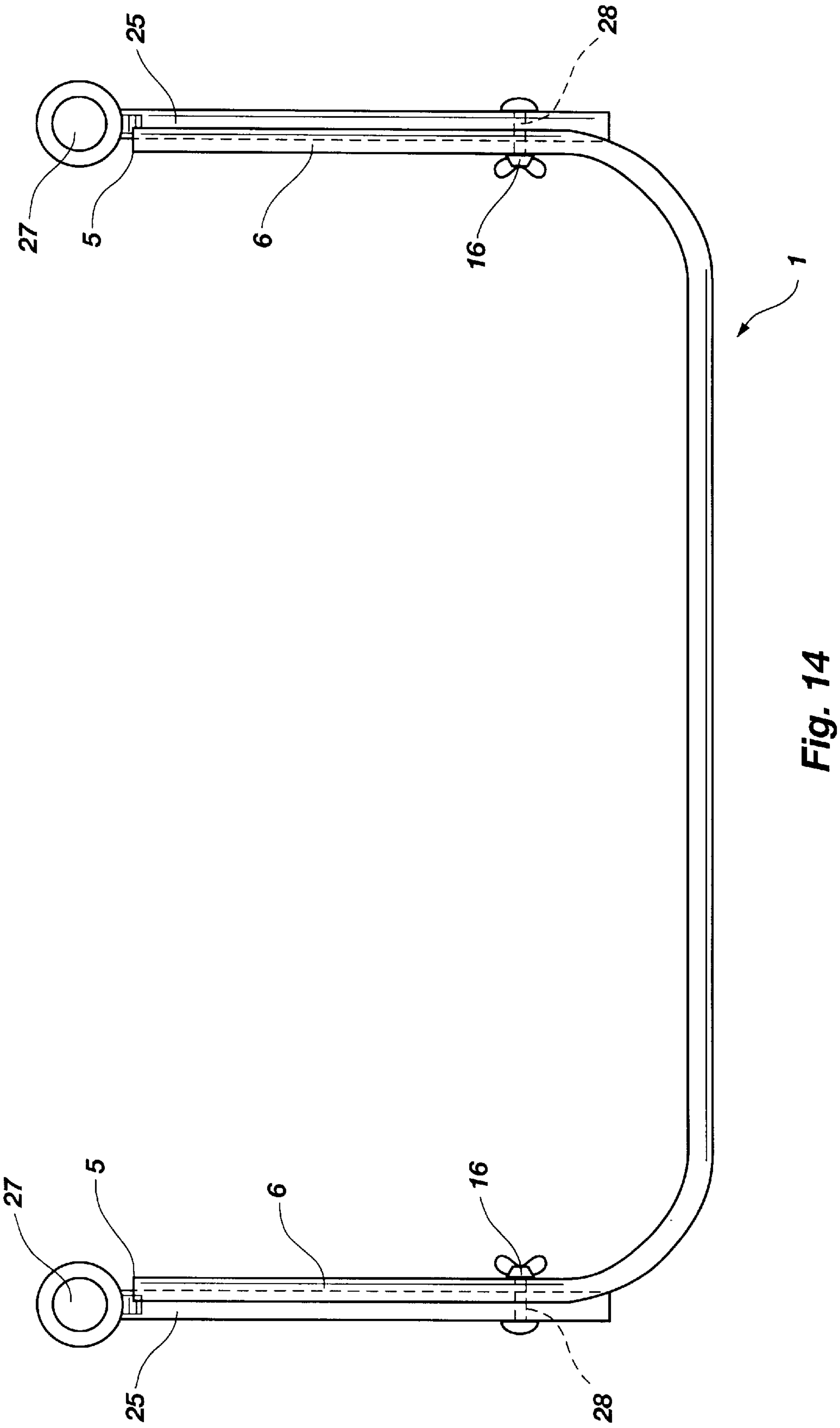
FIG. 14 is an end view of the embodiment of FIG. 13 where the height of the alternate means for attaching the sheet to the base is adjustable.
Figure 15:
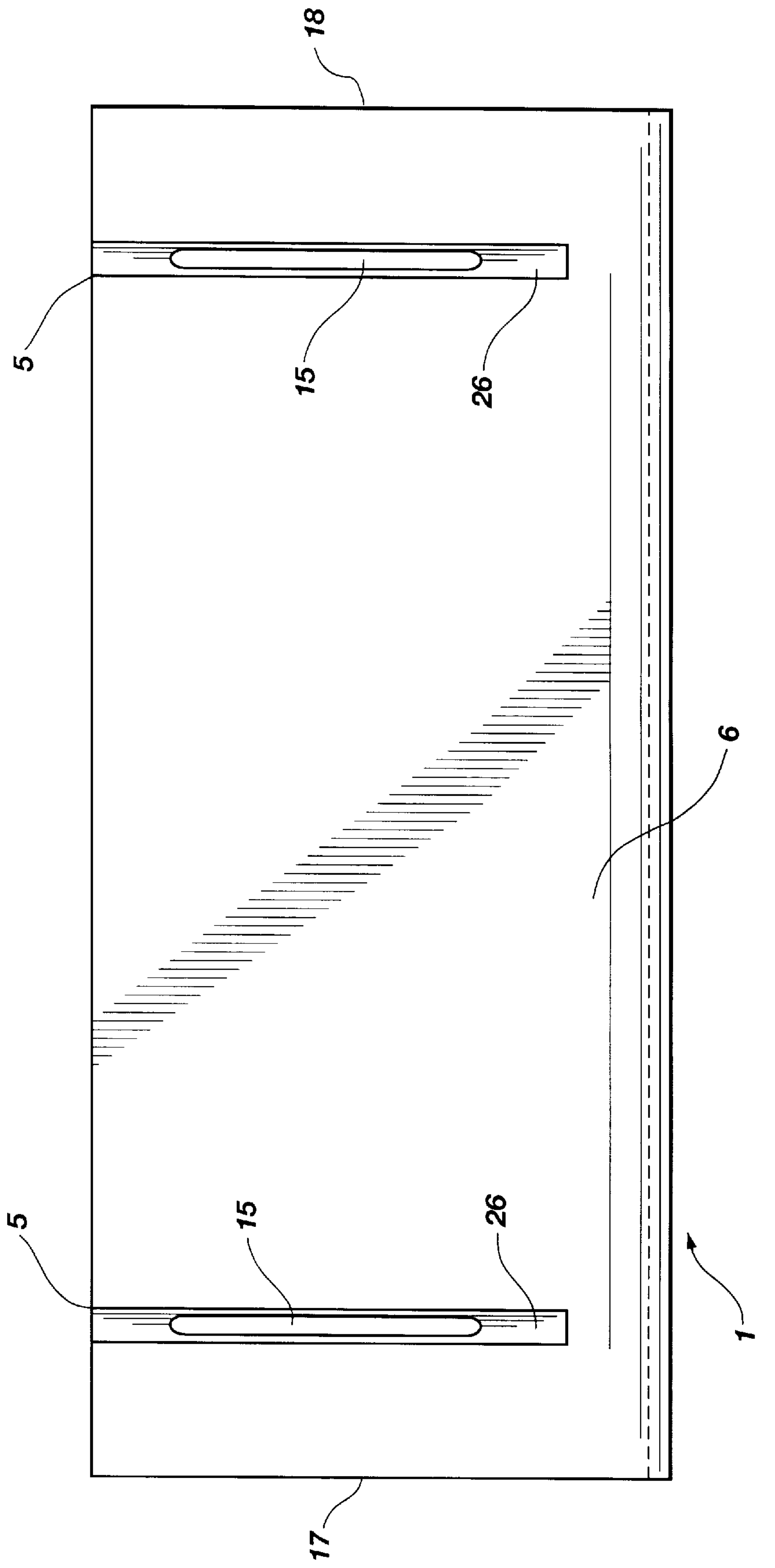
FIG. 15 shows a side view of the base for the embodiment of FIG. 14.
Figure 16:
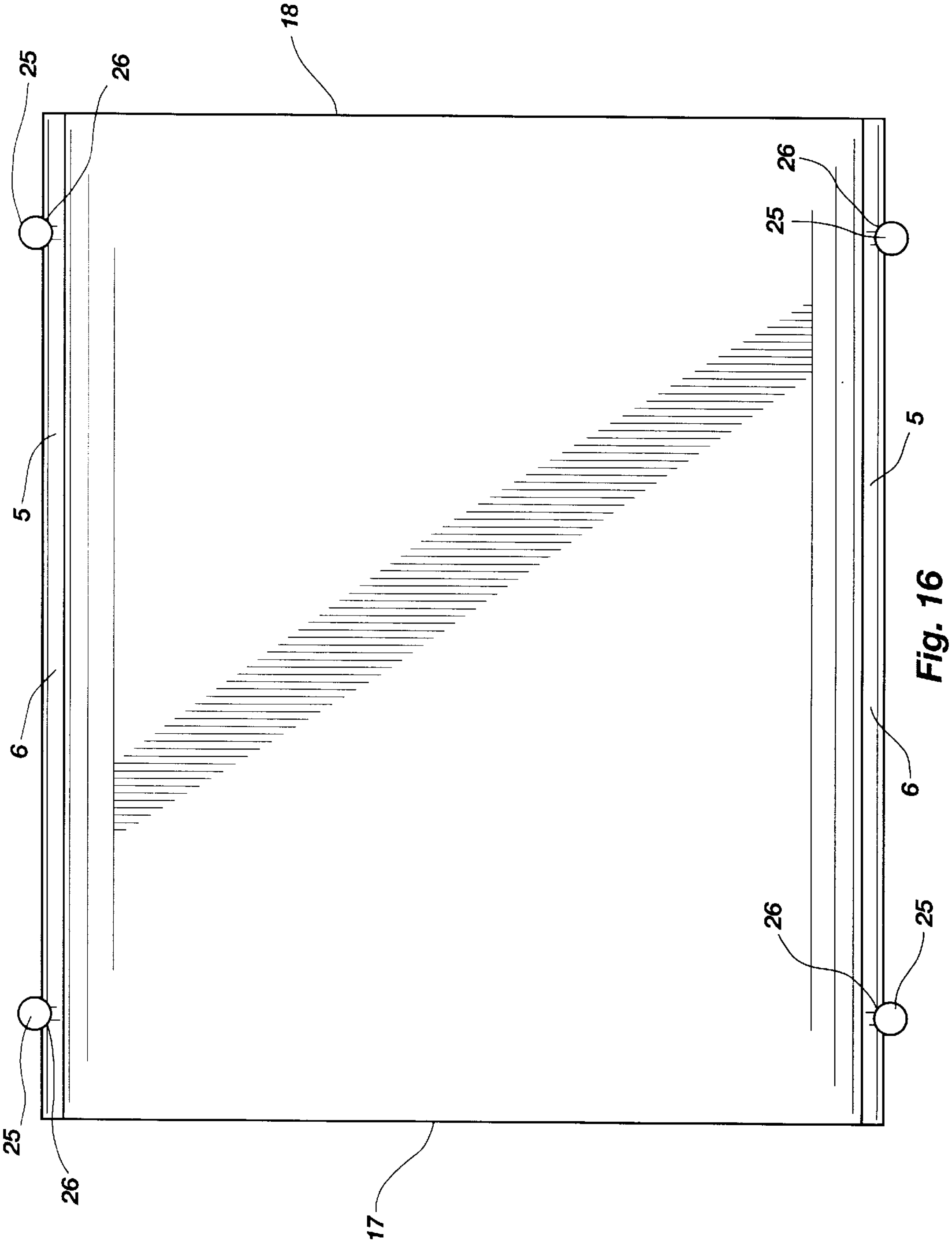
FIG. 16 illustrates, from the top, the base for the embodiment of FIG. 14, where the tops of the vertical columns are not shown.

A version of this first optional embodiment which has the distance between the bottom 14 of the base 1 and the rod 10 adjustable is portrayed in FIG. 10, FIG. 11, and FIG. 12. This is preferably accomplished by having the outer diameter of the bottom 14 smaller than the inner diameter of the sides 6 and having the sides 19, 20 of the bottom 14 curve so that they are essentially parallel to one another and can each slide into one of the hollow sides 6. One or more narrow slits 23 are cut longitudinally along the sides 6 at the end of the sides 6 which attaches to the bottom 14 and running sufficiently far toward the other end of the sides 6 that the end of the sides 6 to which the bottom 14 is attached can be squeezed with sufficient force that the side 6 is precluded from sliding along the bottom 14. The means for squeezing the vertical column is preferably an adjustable clamp 24.

A second optional embodiment of the Support for a Limb of a Body is illustrated in FIG. 13, FIG. 14, FIG. 15, and FIG. 16.

As does the preferred embodiment, this second optional embodiment has a base 1 with a generally U-shaped cross section. To each side 6, two or more pins 25 are slidably but lockably attached, preferably as described below.

In each side 6, two or more generally vertical slots 15 exist to accommodate a releasable fastener 16, such as a bolt and wing nut. Preferably, on the outer side of each slot 15, i.e., the side away from the horizontal portion of the U-shaped base 1, a vertical groove 26 runs along the slot 15 from the top 5 of the side 6 of the U-shaped base 1 to a location below the slot 15.

A pin 25 is placed in each groove 26. Near the top of each pin 25 is a first aperture 27, preferably formed by shaping the upper portion of the pin 25 into a circle. Near the bottom of each pin 25 is a second aperture 28, which is oriented at approximately a ninety-degree angle with respect to the first aperture 28. This second aperture 28 is designed to accommodate a releasable fastener 16, such as a bolt and wing nut. The releasable fastener 16 is simply released to allow the pin 25 to be moved up or down with respect to the side 6; and when the desired distance has been reached, the releasable fastener 16 is again fastened.

The length of the sheet 2 is preferably selected to be less than the distance between the vertical slots 15 on a given side 6, although more than two slots 15 and associated pins 25 could be utilized if the sheet 2 were to contain intermediate apertures (not illustrated) in the longitudinal loops 3 wherever a pin 25 is desired to be located.

In any of the embodiments of the Support for a Limb of a Body, additional loops 3 can be formed intermediate the longitudinal sides 4 of the sheet 2 in order to provide a means for adjusting the amount of sag in the sheet 2.

To install the sheet 2, a rod 10 is removably placed into the first aperture 27 of a pin 25 near the first end 17 or the second end 18 of a side 6. The rod 10 is then removably inserted into one longitudinal loop 3 of the sheet 2. When the rod 10 reaches the other end 18 or 17 of the sheet 2 (or any of the intermediate apertures in the longitudinal loop 3), the rod 10 is removably placed through the first aperture 27 of another pin 25. (Of course, if an intermediate aperture has been employed, the rod 10 is then removably inserted into a more distant portion of the longitudinal loop 3 in the sheet 2; and the process is repeated.)

The preceding process is subsequently conducted for the other side 6 of the base 1 in order to attach the sheet 2 readily, but releasably and securely, to the base 1.

A less elaborate version of the second optional embodiment (not illustrated) eliminates the slots 15, the grooves 26, and the second apertures 28. The pins 25 are simply permanently attached to the sides 6, preferably with tops 5 of the pins 25 at the second end 18 of the sides 6 farther from the bottom 14 of the base 1 than the tops 5 of the pins 25 at the first end 17 of the sides 6.

The dimensions for all embodiments of the Support for a Limb of a Body can be varied to create models that are suitable for individuals of different sizes, such as adults and children.

Figure 17:
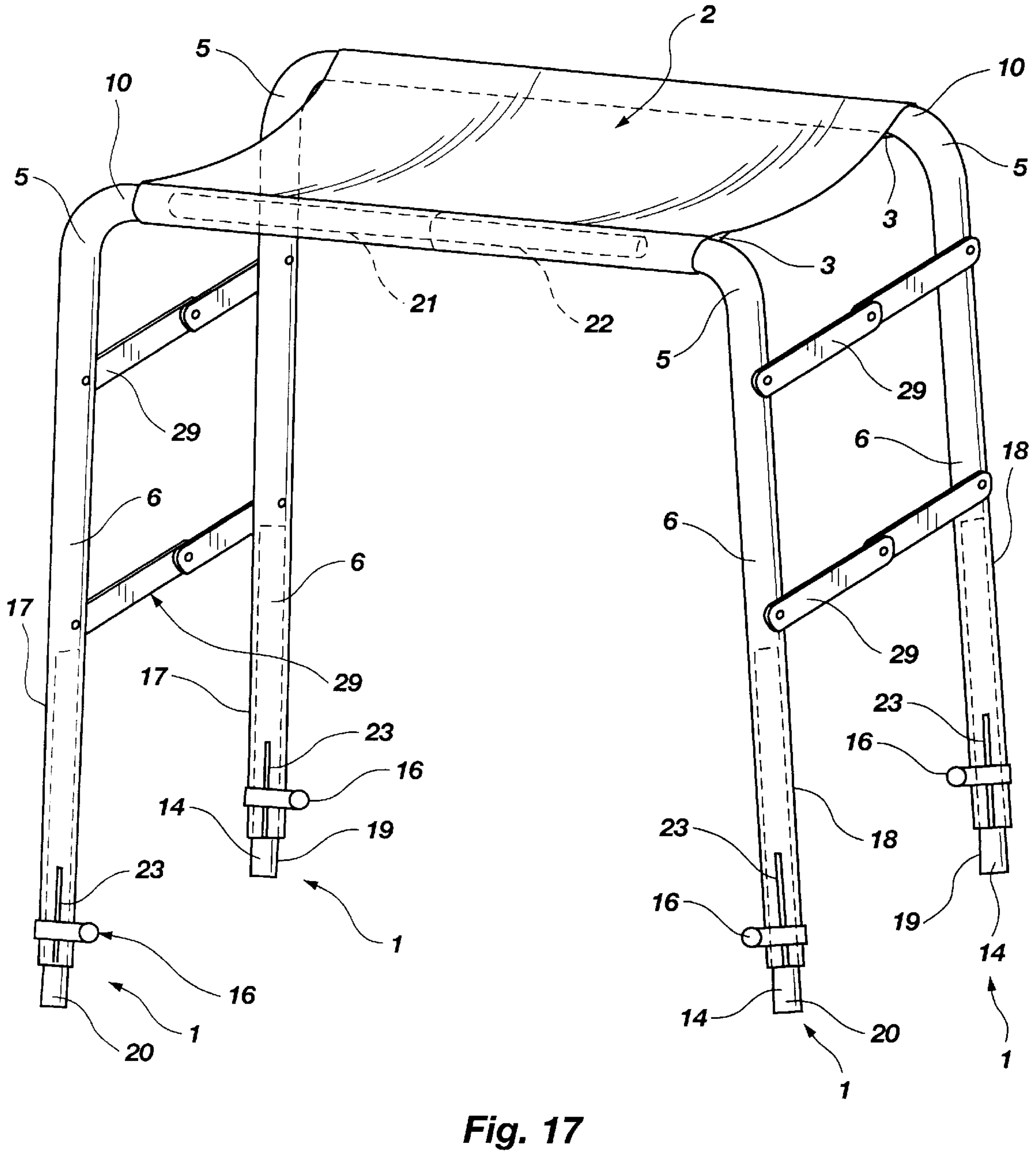
FIG. 17 portrays an optional embodiment similar to that of FIG. 10 except that bracing is used across the ends rather than having the vertical portions of the base connected at the bottom of each end of the base.

A third optional embodiment of the Support for a Limb of a Body is portrayed in FIG. 17.

This embodiment is the same as adjustable version of the first optional embodiment with exception that the portion of the bottom 14 of the base 1 running between the first side 19 and the second side 20 has been eliminated and replaced with one or more hinged braces 29. At the first end 17 of the base 1, one or more hinged braces 29 are connected between the side 6 on the first side 19 of the base 1 and the second side 20 of the base 1. Similarly, at the second end 18 of the base 1, one or more hinged braces 29 are rotatably connected between the side 6 on the first side 19 of the base 1 and the second side 20 of the base 1.

This embodiment would generally be placed on a floor when a user is sitting in a chair. The other embodiments are generally placed upon the same surface on which the user is reclining.

I claim:

1. A support for a limb of a body, which comprises:

a sheet of flexible material having longitudinal sides with loops along each longitudinal side of said sheet;

a base; and a means for utilizing the loops to connect said sheet to said base readily, but releasably and securely, wherein:

the base comprises a bottom, a first end, a second end, a center, and two sides with each of said sides having a top, each of said sides forming with the bottom a generally U-shaped cross section, with a channel having a slot opening toward the center of the base at the top of each side of said base, and the of each side of said base near the second end of said base being farther from the bottom of said base than is the top of each side of said base near the first end of said base;

the means for utilizing the loops to connect said sheet comprises said channels and two rods, one of said rods is inserted into the loop along one longitudinal side of said sheet and the other of said rods is inserted into the loop along the other longitudinal side of said sheet so that one rod and the corresponding loop are inserted into one channel with said sheet extending through the slot of said channel and the other rod and the corresponding loop are inserted into the other channel with said sheet extending through the slot of said channel.

2. A support for a limb of a body, which comprises:

a sheet of flexible material having longitudinal sides with loops along each longitudinal side of said sheet;

a base; and a means for utilizing the loops to connect said sheet to said base readily, but releasably and securely, wherein:

the base comprises a bottom, a first end, a second end, a center, two sides with each of said sides having a top, said bottom and sides forming a generally U-shaped cross section, and two auxiliary sides, each said side having one said auxiliary side slidably and lockably attached to said side and each said auxiliary side having a channel with a slot opening toward the center of the base at the top of each said auxiliary side, and the top of the auxiliary side of said base near the second end of said base being farther from the bottom of said base than is the of each auxiliary side of said base near the first end of said base; and the means for utilizing the loops to connect said sheet comprises said channels and two rods, one of said rods is inserted into the loop along one longitudinal side of said sheet and the other of said rods is inserted into the loop along the other longitudinal side of said sheet so that one rod and the corresponding loop are inserted into one channel with said sheet extending through the slot of said channel and the other rod and the corresponding loop are inserted into the other channel with said sheet extending through the slot of said channel.

3. A support for a limb of a body, which comprises:

a sheet of flexible material having longitudinal sides with loops along each longitudinal side of said sheet;

a base; and a means for utilizing the loops to connect said sheet to said base readily, but releasably and securely, wherein:

the base comprises a bottom, a first end, a second end, a center, two sides with each of said sides having a top, said bottom and sides forming a generally U-shaped cross section, and two auxiliary sides, each said side having one said auxiliary side slidably and lockably attached to said side and each said auxiliary side having a channel with a slot opening toward the center of the base at the top of each said auxiliary side, and the top of each auxiliary side of said base near the second end of said base being farther from the bottom of said base than is the top of each auxiliary side of said base near the first end of said base;

the means for utilizing the loops to connect said sheet comprises said channels and two rods, one of said rods is inserted into the loop along one longitudinal side of said sheet and the other of said rods is inserted into the loop along the other longitudinal side of said sheet so that one rod and the corresponding loop are inserted into one channel with said sheet extending through the slot of said channel and the other rod and the corresponding loop are inserted into the other channel with said sheet extending through the slot of said channel.

* * * * *